(12) United States Patent
Basaric et al.

(10) Patent No.: US 8,022,097 B2
(45) Date of Patent: Sep. 20, 2011

(54) ADAMANTANE-DIPYRROMETHANE DERIVATIVES, METHOD OF PREPARATION AND APPLICATIONS IN ANION SENSING

(75) Inventors: Nikola Basaric, Zagreb (HR); Marija Aleskovic, Zagreb (HR); Kata Majerski, Zagreb (HR)

(73) Assignee: Rudjer Boskovic Institute, Zagreb (HR)

( * ) Notice: Subject to any disclaimer, the term of this patent is extended or adjusted under 35 U.S.C. 154(b) by 0 days.

(21) Appl. No.: 12/560,774

(22) Filed: Sep. 16, 2009

(65) Prior Publication Data

US 2010/0069648 A1    Mar. 18, 2010

Related U.S. Application Data

(63) Continuation of application No. PCT/HR2008/000008, filed on Mar. 12, 2008.

(30) Foreign Application Priority Data

Mar. 16, 2007 (HR) .............................. P 20070111 A

(51) Int. Cl.
*C07D 403/06* (2006.01)
*C07D 403/08* (2006.01)
*A61K 31/4025* (2006.01)

(52) U.S. Cl. ........................................ 514/422; 548/518
(58) Field of Classification Search .................. None
See application file for complete search history.

(56) References Cited

U.S. PATENT DOCUMENTS

| | | | |
|---|---|---|---|
| 5,512,675 | A | 4/1996 | Tang et al. |
| 5,599,948 | A | 2/1997 | Wijesekera |
| 5,767,272 | A | 6/1998 | Wijesekera et al. |
| 6,924,375 | B2 | 8/2005 | Lindsey et al. |
| 7,022,862 | B2 | 4/2006 | Lindsey et al. |
| 7,148,361 | B2 | 12/2006 | Lindsey et al. |
| 7,323,561 | B2 | 1/2008 | Lindsey et al. |
| 7,501,507 | B2 | 3/2009 | Balakumar et al. |

FOREIGN PATENT DOCUMENTS

| | | |
|---|---|---|
| EP | 0665230 A2 | 8/1995 |
| WO | 03027066 A2 | 4/2003 |

OTHER PUBLICATIONS

Best, et al.; "Abiotic Guanidinium Containing Receptors for Anionic Species"; Coordination Chemistry Reviews 240 (2003) pp. 3-15.
Renic, et al.; "Adamantane-Dipyrromethanes: Novel Anion Receptors"; Tetrahedron Letters 48 (2007) pp. 7873-7877.
Gale; "Amidopyrroles: From Anion Receptorsto Membrane Transport Agents"; Chem. Commun., (2005). pp. 3761-3772.
Llinares, et al.; "Ammonium Based Anion Receptors"; Coordination Chemistry Reviews 240 (2003) pp. 57-75.
Gale; "Anion and Ion-Pair Receptor Chemistry: Highlights from 2000 and 2001"; Coordination Chemistry Reviews 240 (2003) pp. 191-221.
Beer, et al.; "Anion Recognition and Sensing: The State of the Art and Future Perspectives"; Angew. Chem. Int. ed. (2001) 40 pp. 486-516.
Baeyer, A., Ber. Dtsch. Chem. Ges. (1886), 19, pp. 2184-2185.
Frank, Michael et al: "Dinuclear RuII and/or OsII complexes of bis-bipyridine bridging ligands containing adamantane spacers: synthesis, luminescence properties, intercomponent energy and electron transfer processes" Inorganica Chimica Acta, 242(1-2), 281-91'CODEN: ICHAA3; ISSN: 0020-1693, 1996, XP002490276 p. 283; compound 2.
Martinez-Màñez, et al.; "Fluorogenic and Chromogenic Chemosensors and Reeagents for Anions"; Chem. Rev. (2003) 103 pp. 4419-4476.
International Preliminary Report on Patentability; PCT/HR2008/000008; Jun. 30, 2009; 12 pages.
International Search Report; PCT/HR2008/000008; Jul. 30, 2008; 2 pages.
Callan, et al.; "Luminescent Sensors and Switches in the Early 21st Century"; Tetrahedron 61 (2005) pp. 8551-8588.
Choi, et al.; "Macrocyclic Anion Receptors Based on Directed Hydrogen Bonding Interactions"; Coordination Chemistry Reviews 240 (2003) pp. 101-110.
Hosseini; "Molecular Tectonics: From Molecular Recognition of Anions to Molecular Networks"; Coordination Chemistry Reviews 240 (2003) pp. 157-166.
Wedge, et al.; "Multidentate Carborane-Containing Lewis Acids and Their Chemistry: Mercuracarborands"; Coordination Chemistry Reviews 240 (2003) pp. 111-128.
Littler, et al.; Refined Sunthesis of 5-Substituted Dipyrromethanes; J. Org. Chem. (1999) 64 pp. 1391-1396.
Prasanna de Silva, et al.; "Signaling Recognition Events with Fluorescent Sensors and Switches"; Chem. Rev. (1997) 97 pp. 1515-1566.
Davis, et al.; "Steroids as Organising Elements in Anion Receptors" Coordination Chemistry Reviews 240 (2003) pp. 143-156.
Gale; "Structural and Molecular Recognition Studies with Acyclic Anion Receptors"; Acc. Chem. Res. 2006, 39, pp. 465-475.
Kar, Ari K. et al: "Synthesis of bilin-1,19-diones and biladiene-ac-1,19-diones with C(10) adamantyl and tert-butyl groups" Journal of Heterocyclic Chemistry, 35(4), 795-803 CODEN: JHTCAD; ISSN: 0022-152X, 1998, XP002490277.
Dong-Hoon Won, et al.; "Synthesis of Oligopyrrolic Cluster Bearing Thiophene Spacer as Potential Anion Receptors"; Tetrahedron Letters 44 (2003) pp. 6695-6697. Lambert, et al.; "Synthetic Receptors for Phospholipid Headgroups"; Coordination Chemistry Reviews 240 (2003) pp. 129-141.
Beer, et al.; "Transition Metal and Organmetallic Annion Complexation Agents"; Coordination Chemistry Reviews 240 (20030 pp. 167-189, 2001.
Amendola, et al.; "What Anions Do to N-H-Containing Receptors"; Acc. Chem. Res. (2006) 39 pp. 343-353.

*Primary Examiner* — Yong Chu
*Assistant Examiner* — Michael Barker
(74) *Attorney, Agent, or Firm* — Nixon Peabody LLP; Jeffrey L. Costellia

(57) ABSTRACT

Aamantane dipyrromethane derivatives are obtained by reacting adamantane carbonyl derivatives with pyrrole or pyrrole derivative, in the presence of acid. Adamantane-dipyrromethanes are used to bind anions of the group consisting of: F—, Cl—, Br—, acetate, HSO4-NO3-, and H2PO4-, and particularly F—.

12 Claims, 2 Drawing Sheets

ADAMANTANE-DIPYRROMETHANE DERIVATIVES, METHOD OF PREPARATION AND APPLICATIONS IN ANION SENSING

CROSS-REFERENCE TO RELATED APPLICATIONS

The present application is a continuation of pending International patent application PCT/HR2008/000008 filed on Mar. 12, 2008, which designates the United States and claims priority from Croatian patent application P20070111A filed on Mar. 16, 2007. The content of both prior applications is incorporated herein by reference.

FIELD OF THE INVENTION

This invention relates to adamantane derivatives, a process for their preparation, and use of the compounds presented herein for anion sensing, anion extraction, and as intermediates in the synthesis of anion sensors.

BACKGROUND OF THE INVENTION

Dipyrromethanes are compounds known for more than a century (Baeyer, A., *Ber. Dtsch. Chem. Ges.* 1886, 19, 2184). Dipyrromethanes were substituted (U.S. Pat. Nos. 6,924,375, and 5,599,948) and used as intermediates for the synthesis of calixpyrroles, porphyrines (U.S. Pat. Nos. 7,501,507, 7,323, 561, 7,148,361 and 5,767,272; WO 03/027066 A2 (Apr. 3, 2003); and EP 0 665 230 A2 (Aug. 2, 1995)) and expanded porphyrines (U.S. Pat. No. 5,512,675). However, only recently a reliable synthetic method for their preparation was reported (U.S. Pat. No. 7,022,862); and Litter, B. J.; Miller, M. A.; Hung, C.-H.; Wagner, R. W.; O'Shea, D. F.; Boyle, P. D.; Lindsey, J. S. *J. Org. Chem.* 1999, 64, 1391-1396).

In U.S. Pat. No. 7,022,862, Lindsey et al. describe a process for the preparation of dipyrromethanes wherein pyrrole derivative is coupled with an appropriate carbonyl derivative in the presence of acid. In the '862 patent, the carbonyl derivative is comprised of aromatic and aliphatic aldehydes and ketones, but not adamantane derivatives, the subject of this invention. In addition, the use of dipyrromethanes as anion binding reagents and intermediates for anion sensors is not described by the '862 patent. Only Kar and Lightner describe a compound in which the adamantane moiety is attached to dipyrromethane (*Heterocycl. Chem.* 1998, 35, 795-803). The described adamantane-dipyrromethane is a bilivedrin derivative, but its use for binding anions has not been reported.

Adamantane derivatives are characterized by lipophilicity which ensures the solubility of adamantane-dipyrromethanes in organic solvents and provides the applicability of adamantane-dipyrromethanes as anion extracting agents. Anions play a key role in chemical and biological processes. Many anions act as nucleophiles, bases, redox agents or phase transfer catalysts, while most enzymes bind anions as either substrates or cofactors. Additionally, it is of great importance to detect anionic pollutants, such as phosphates and nitrates in ground water. Consequently, it is highly desirable to obtain new anion sensors which would be characterized by higher binding constants and selectivity. This demand has inspired research during the last 20 years which has resulted in numerous publications (e.g. *Chem. Rev.* 1997, 97, 1515-1566; *Angew. Chem. Int. Ed.* 2001, 40, 486-516; *Coord. Chem. Rev.* 2003, 240, issues 1-2; Chem. Rev. 2003, 103, 4419-4476; *Top. Curr. Chem.* 2005, 255; *Chemm. Commun.*, 2005, 3761-3772; *Tetrahedron*, 2005, 61, 8551-8588; *Acc. Chem. Res.* 2006, 39, 343-353; and *Acc. Chem. Res.* 2006, 39, 465-475). A significant number of molecules which are used as anion sensors are composed of pyrrole subunits. Namely, pyrrole has an acidic NH proton to which anion can be attached by hydrogen bonds. Among these molecules, anion sensing has been reported for the derivatives of amidopyrroles, calixpyrroles, sapphyrines and porphyrines, as well as dipyrroquinoxalines.

In all the mentioned molecules, binding of the anion is accomplished by the presence of two or more NH-anion hydrogen bonds. The presence of two NH protons is sufficient to accomplish binding of an anion with sufficient binding constants (as in the case of dipyrroquinoxalines), thus prompting investigation of the applicability of dipyrromethanes as anion sensors.

SUMMARY OF THE INVENTION

The present invention provides new adamantane-dipyrromethane derivatives, their method of preparation, intermediates used in the process of preparation, as well as their use as anion binding reagents for $F^-$, $Cl^-$, $Br^-$, acetate, $HSO_4^-$, $NO_3^-$ and $H_2PO_4^-$.

DETAILED DESCRIPTION OF THE INVENTION

Figure 1:
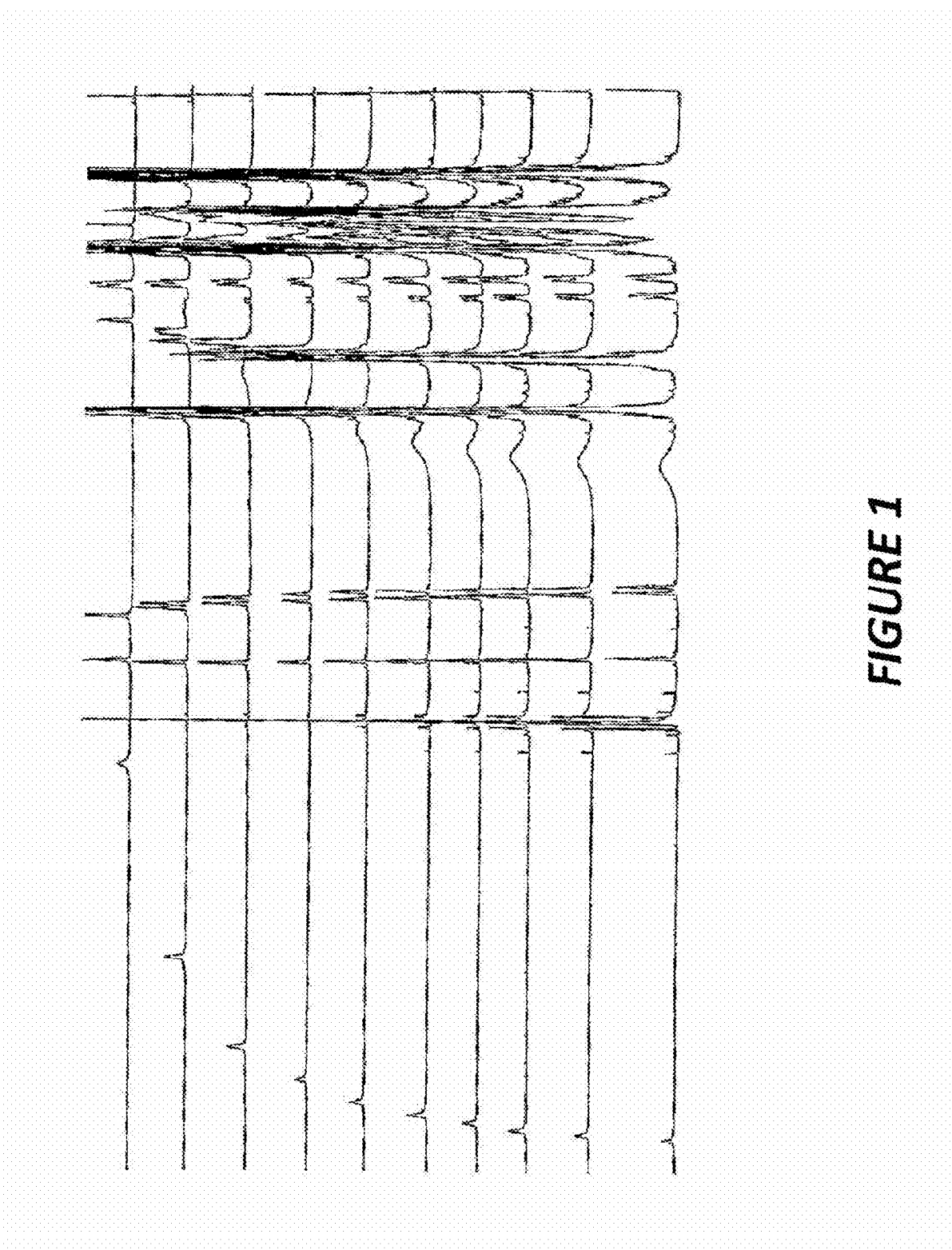
FIG. 1 illustrates $^1H$ NMR spectra ($CDCl_3$) of adamantane-dipyrromethane of general formula I, wherein $R_2$, $R_3$=pyrrole-2-yl and $R_1$, $R_4$-$R_9$=H (c=0.05 M) with increasing concentrations of $Bu_4NF$ (added as 1 M solution in THF).

The subject of this invention is adamantane-dipyrromethane derivatives presented by general formula I:

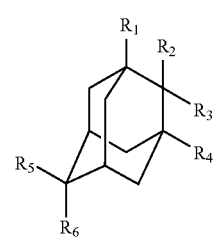

wherein $R_1$, $R_2$, $R_3$, $R_4$, $R_5$, and $R_6$ are as follows:

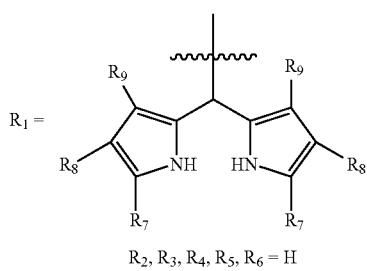

$R_2, R_3, R_4, R_5, R_6 = H$

-continued

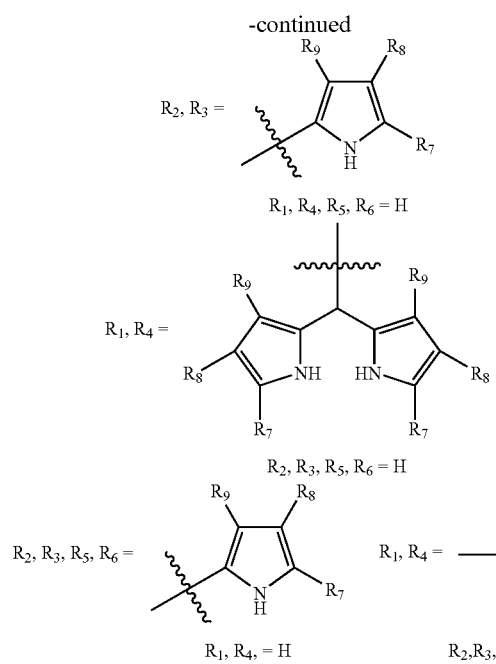

In other words: $R_1$-$R_6$ are defined as follows:

$R_1$ is dipyrromethane or substituted dipyrromethane, and $R_2$, $R_3$, $R_4$, $R_5$ and $R_6$ are hydrogen, or $R_2$, $R_3$ are the same pyrrole or substituted pyrrole, and $R_1$, $R_4$, $R_5$ and $R_6$ are hydrogen, or $R_1$ and $R_4$ are the same dipyrromethane or substituted dipyrromethane and $R_2$, $R_3$, $R_4$, $R_5$ and $R_6$ are hydrogen, or $R_2$, $R_3$, $R_5$ and $R_6$ are the same pyrrole or substituted pyrrole, and $R_1$, and $R_4$ are hydrogen; or $R_1$ and $R_4$ are a carbonyl group, and $R_2$, $R_3$, $R_4$, $R_5$ and $R_6$ are hydrogen.

In the pyrrole or substituted pyrrole, $R_7$, $R_8$, and $R_9$ are hydrogen, methyl, ethyl, propyl, butyl, pentyl, hexyl, vinyl, Cl, Br, CN, CHO, $CH_2OH$, $COOR_{10}$ or aryl, or their combination, and $R_{10}$ is hydrogen, methyl, ethyl, tert-butyl, phenyl and benzyl. The aryl, if it is present in the compound, has the following formula:

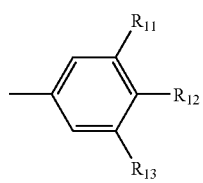

and wherein $R_{11}$, $R_{12}$, $R_{13}$ is hydrogen, methyl, ethyl, propyl, methoxy, CN, F, Cl, and Br or their combination.

The subject of the invention is, furthermore, a 2-step process of preparation of adamantane-dipyrromethane derivatives, wherein the first step comprises of condensation of adamantane carbonyl derivative with pyrrole or pyrrole derivative under acid conditions, and the second step comprises of isolation of adamantane dipyrromethane from the reaction mixture. The steps are further defined in the general procedure of the preparation.

Adamantane derivatives defined herein comprise of adamantane-2-one, adamantane-1-carbaldehyde, adamantane-1,3-dicarbaldehyde and adamantane-2,6-dione. The step of isolation described herein comprises of removal of acid by extraction using a water solution of a base, extraction with an organic solvent, removal of the solvent and/or pyrrole by distillation, purification by chromatography, and/or crystallization. The reaction is carried out according to the following general reaction scheme:

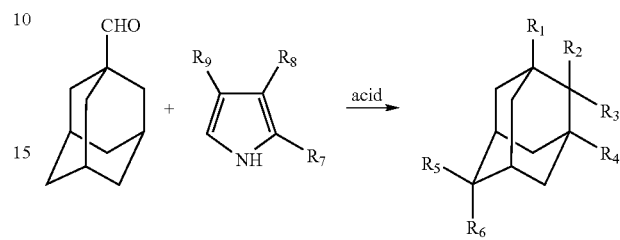

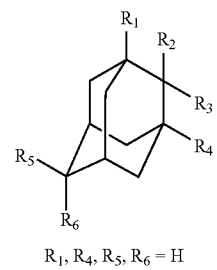

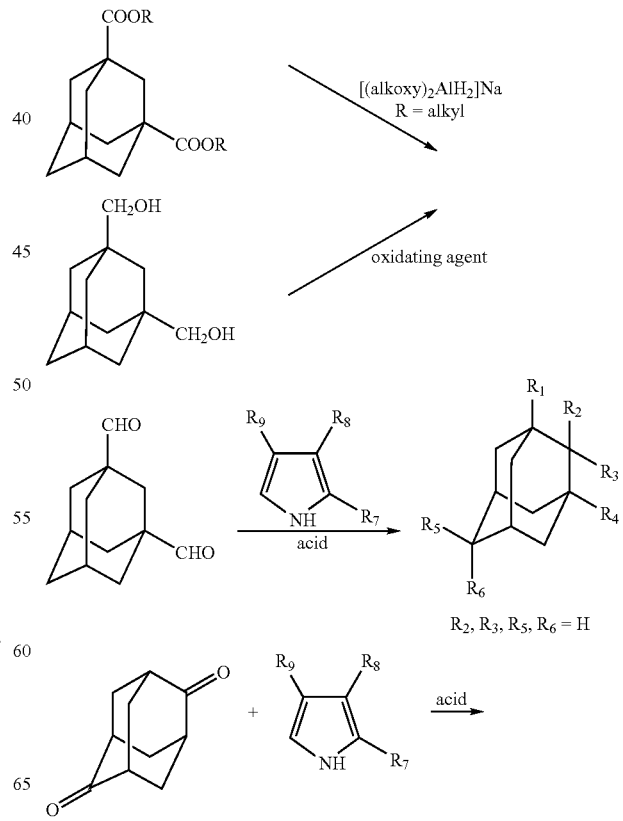

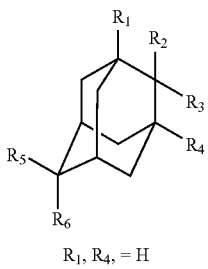

R₁, R₄, = H

General procedure for the preparation of Adamantane-dipyrromethanes

In a reaction vessel under a stream of N₂ or Ar, one equivalent of adamantane-carbonyl derivative is dissolved in excess of pyrrole or pyrrole derivative presented in the general reaction scheme above and organic solvent. To the reaction mixture, 0.1 equivalent of acid was added and the mixture was stirred at room temperature or elevated temperature for at least one hour. The progress of the reaction was followed by TLC on silica gel using $CH_2Cl_2$, $CH_2Cl_2$/hexane, hexane/ethyl acetate, hexane/diethyl ether or $CH_2Cl_2/CH_3OH$ as an eluent. Upon disappearance of the starting carbonyl derivative, the reaction was quenched by the addition of an aqueous solution of base. To the mixture was added appropriate organic solvent not mixable with water, particularly $CH_2Cl_2$, and the layers were separated. The aqueous layer was extracted two more times using the appropriate organic solvent; organic extracts were washed with water, collected and dried over anhydrous $CaCl_2$, $K_2CO_3$, or $Na_2SO_4$ and particularly $MgSO_4$. After filtration, the solvent was removed by distillation under reduced pressure, and wherein applicable, the excess pyrrole was also removed by a distillation under reduced pressure. The obtained crude product after distillation was chromatographed on a column filled with silica gel using $CH_2Cl_2$, $CH_2Cl_2$/diethyl ether, hexane/diethyl ether or hexane/ethyl acetate, as an eluent.

The invention also embodies an intermediate in the preparation of some of the adamantane-dipyrromethanes presented herein, the carbonyl compound, adamantane-1,3-dicarbaldehyde and the process of preparing it.

Adamantane-1,3-dicarbaldehyde may be prepared by two independent routes which are:

a) reduction of diester of adamantane-1,3-dicarboxylic acid wherein R represents an alkyl group

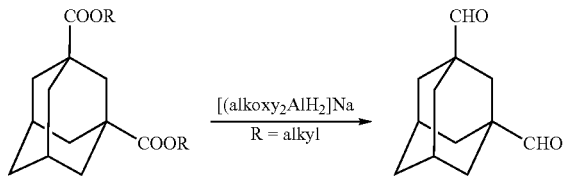

or
b) oxidation of 1,3-bis(hydroxymethyl)adamantane as shown below.

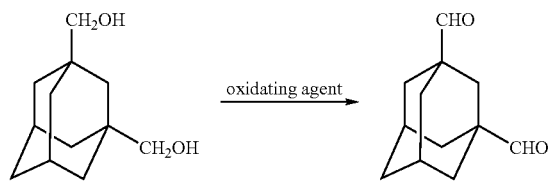

Preparation of adamantane-1,3-dicarbaldehyde—general procedure according route a):

To a solution of diester of adamantane-1,3-dicarboxylic acid (1 equivalent) in an appropriate anhydrous solvent comprising THF or diethyl ether, cooled to −60° C., a suspension of [(alkoxy)₂AlH₂]Na (4 equivalents) in an appropriate anhydrous organic solvent comprising THF or diethyl ether is added. After stirring for at least 1 hour, diluted acid is added. The reaction mixture is warmed and extracted with appropriate organic solvent comprising $CH_2Cl_2$, $CHCl_3$, diethyl ether or ethyl acetate. Combined organic phases were washed with a saturated aqueous solution of NaCl and dried over anhydrous drying agent comprising $CaCl_2$, $K_2CO_3$, $Na_2SO_4$ and particularly $MgSO_4$. After filtration, solvent was evaporated to give the crude product (~40%). The crude product is purified using chromatography on silica gel using pentane/diethyl ether as solvent.

Preparation of adamantane-1,3-dicarbaldehyde—general procedure according route b):

To a suspension of oxidizing agent comprising chromic acid, $MnO_2$, or PCC (4 equivalents) in a suitable solvent comprising $CH_2Cl_2$, $CHCl_3$, THF, or diethyl ether, and particularly $CH_2Cl_2$, is added a suspension of 1,3-bis(hydroxymethyl)adamantane (1 equivalent) in a suitable organic solvent. The reaction mixture is stirred at room temperature or elevated temperature over at least one hour, whereupon it is diluted with anhydrous organic solvent comprising THF or diethylether, and particularly diethyl ether, and filtered through a plug of florisil. The filtrate is evaporated in vacuo to afford dialdehyde (95%). Because of the instability, the isolated dialdehyde is used in the next step without further purification.

Another embodiment of the invention is the use of the herein described compounds for binding anions. Compounds of the invention bind $F^−$, $Cl^−$, $Br^−$, acetate, $HSO_4^−$, $NO_3^−$, and $H_2PO_4^−$ and particularly $F^−$. Binding of the said anions is demonstrated by NMR titrations and illustrated in example 7. The binding is evidenced by the disappearance of the signal of the free NH protons and appearance of a new signal at lower magnetic field which was assigned to the bound NH protons, in a fast exchange with the unbound NH resonances. With increasing concentration of anion, this signal shifted to the lower magnetic field, reaching the maximum value at ~12 ppm.

The described compounds presented by general formula I are intermediates in the synthesis of calixpyrroles, and compounds labeled with at least one fluorescent or chromogenic group that are used as anion indicators. Use of adamantane-dipyrromethanes as intermediates in the synthesis of calixphyrrines is illustrated in example 8.

The compounds, presented by general formula I, their mixtures and compositions containing at least one of compounds herein presented are used as anion extracting agents.

Example 1

1-Di(pyrrole-2-yl)methyladamantane: Obtained by reacting adamantane-1-carbaldehyde (222 mg, 1.36 mmol) with pyrrole (3.65 g, 55 mmol, 3.8 mL) in the presence of TFA (10 μL, 0.14 mmol). After stirring over 1 hour at room temperature, the reaction was quenched and worked-up following the general procedure. After chromatography, reaction furnished 207 mg (51%) of the product in the form of colorless crystals, which were further purified by recrystallisation from benzene/hexane mixture to remove the traces of unreacted pyrrole. Colorless crystals, mp 168-169° C.; ¹H NMR (CDCl₃) δ/ppm (600 MHz) 1.56-1.69 (m, 12H), 1.97 (br.s, 3H), 3.57

(s, 1H), 6.08-6.23 (m, 4H), 6.60-6.69 (m, 2H), 7.97 (br.s, 2H); $^{13}$C NMR (CDCl$_3$) δ/ppm (150 MHz) 28.6 (d, 3C), 36.7 (t, 3C), 36.9 (s, 1C), 40.4 (t, 3C), 51.4 (d, 1C), 106.5 (d, 2C), 108.2 (d, 2C), 115.7 (d, 2C), 130.1 (s, 2C); IR (KBr) ν$_{max}$/cm$^{-1}$ 3369 (s), 2927 (m), 2903 (m), 2864 (m); MS m/z (%) 279 (100, M-H$^+$); HRMS, calculated for C$_{19}$H$_{23}$N$_2$ 279.1861; observed 279.1859.

Example 2

2,2-Di(pyrrrole-2-yl)adamantane: Obtained by reacting adamantane-2-one (250 mg, 1.66 mmol) with pyrrole (4.47 g, 66 mmol, 4.6 mL) in the presence of TFA (13 µL, 0.17 mmol). After stirring over 1.5 hours at room temperature the reaction was quenched and worked-up following the general procedure. After chromatography, reaction furnished 143 mg of the product in the form of colorless crystals which were further purified by rechromatography to yield 128 mg (29%). Colorless crystals, mp 183.4-185.2° C.; $^1$H NMR (CDCl$_3$) δ/ppm (300 MHz) 1.69-1.87 (m, 8H), 2.16-2.26 (m, 4H), 2.64 (br.s, 2H), 6.04-6.07 (m, 4H), 6.56-6.58 (m, 2H), 7.78 (br. s, 2H); $^{13}$C NMR (CDCl$_3$) δ/ppm (75 MHz) 27.3 (d, 2C), 33.6 (t, 4C), 33.9 (d, 2C), 38.1 (t, 1C), 45.0 (s, 1C), 103.9 (d, 2C), 107.3 (d, 2C), 116.1 (d, 2C), 137.9 (s, 2C); IR (KBr) ν$_{max}$/cm$^{-1}$ 3382 (s), 3097 (w), 2950 (m), 2924 (m), 2890 (m), 2894 (m), 1107 (m), 1028 (m), 787 (m), 727 (s); MS m/z (%): 265 (100, M-H$^+$); HRMS, calculated for C$_{18}$H$_{21}$N$_2$ 265.1705; observed 265.1706; Anal. Calcd. For C$_{18}$H$_{22}$N$_2$: C, 81.16; H, 8.32; N, 10.52. Found C, 81.17; H, 7.60; N, 10.71.

Example 3

1,3-Bis[di(pyrrole-2-yl)methyl]adamantane: Obtained by reacting adamantane-1,3-dicarbaldehyde (244 mg, 1.27 mmol) with pyrrole (6.82 g, 102 mmol, 7.05 mL) in the presence of TFA (9.4 µL, 0.12 mmol). After stirring over 1.5 hours at room temperature the reaction was quenched and worked-up following the general procedure. After chromatography (eluting with CH$_2$Cl$_2$ and by increasing polarity by the addition of diethyl-ether, up to 20%), reaction furnished 200 mg (37%) of the product in the form of colorless crystals which were further purified by recrystallization from the benzene/hexane mixture and dried on high vacuum. Colorless crystals, mp 110-112° C.; $^1$H NMR (CDCl$_3$) S/ppm (300 MHz) 1.38-1.55 (m, 12H), 1.96-2.02 (m, 4H), 3.57 (br.s, 2H), 6.00-6.19 (8H), 6.58-6.65 (m, 4H), 7.94 (br.s, 4H); $^{13}$C NMR (CDCl$_3$) δ/ppm (75 MHz) 28.8 (d, 2C), 35.8 (t, 1C), 37.8 (s, 2C), 39.3 (t, 4C), 43.8 (t, 1C), 50.9 (d, 2C), 106.5 (d, 4C), 108.2 (d, 4C), 115.8 (d, 4C), 129.9 (s, 4C); IR (KBr) ν$_{max}$/cm$^{-1}$ 3382 (s), 2901 (s), 2847 (m), 720 (s); MS m/z (%): 423 (100, M-H$^+$); HRMS, calculated for C$_{28}$H$_{31}$N$_4$ 423.2549; observed 423.2542.

Example 4

2,2,6,6-Tetra(pyrrole-2-yl)adamantane: Obtained by reacting adamantane-2,6-dione (200 mg, 1.2 mmol) with pyrrole (6.44 g, 96 mmol, 6.6 ml) in the presence of TFA (9 µl, 0.12 mmol). After stirring over 1.5 hours at room temperature, the reaction was quenched and worked-up following the general procedure. After chromatography (eluting with CH$_2$Cl$_2$ and by increasing polarity by the addition of diethyl-ether, up to 20%), reaction furnished 75 mg (15%) of the crude product in the form of colorless crystals which were further purified by recrystallisation. Colorless crystals, decomposition above 215° C.; $^1$H NMR (DMSO-d$_6$) δ/ppm (300 MHz) 1.83-1.95 (m, 8H), 2.68 (br.s, 4H), 5.73-5.86 (m, 8H), 6.42-6.50 (m, 4H), 10.09 (br.s, 4H); $^{13}$C NMR (DMSO-d$_6$) S/ppm (75 MHz) 29.2 (t, 4C), 31.2 (d, 4C), 44.3 (s, 2C), 103.7 (d, 4C), 106.5 (d, 4C), 115.2 (d, 4C), 138.2 (s, 4C); IR (KBr) ν$_{max}$/cm$^{-1}$ 3409 (s), 3379 (s), 2959 (m), 2925 (m), 2899 (m), 2861 (m), 720 (s); MS m/z (%): 395 (75, M-H$^+$), 328 (100); HRMS, calculated for C$_{26}$H$_{27}$N$_4$ 395.2236; observed 395.2236.

Example 5

2,2-Di(5-phenylpyrrole-2-yl)adamantane: Obtained by reacting adamantane-2-one (107 mg, 0.71 mmol) with 2-phenylpyrrole (102 mg, 0.71 mmol) in the presence of TFA (3 µL, 0.7 mmol) in 20 mL of toluene. The reaction mixture was heated at the temperature of reflux over 20 h, was quenched and worked-up following the general procedure. After chromatography reaction furnished 30 mg (14%) of the product in the form of colorless crystals. $^1$H NMR (CDCl$_3$) δ/ppm (300 MHz) 1.53-1.87 (m, 8H), 2.25-2.30 (m, 4H), 2.72 (br. s, 2H), 6.14 (dd, 2H, J=2.9, J=3.0 Hz), 6.36 (dd, 2H, J=2.9, J=3.0 Hz), 7.11 (t, 2H, J=7.3 Hz), 7.27 (d, 4H, J=7.8 Hz), 7.34 (dd, 4H, J=7.3, J=7.8 Hz), 7.98 (br. s, 2H); $^{13}$C NMR (CDCl$_3$) δ/ppm (75 MHz) 27.3 (d, 2C), 33.6 (t, 4C), 33.8 (d, 2C), 38.0 (t, 1C), 45.3 (s, 1C), 105.6 (d, 2C), 106.2 (d, 2C), 123.3 (d, 4C), 125.6 (d, 2C), 128.6 (d, 4C), 130.5 (s, 2C), 132.7 (s, 2C), 139.0 (s, 2C).

Example 6

Adamantane-1,3-dicarbaldehyde

Procedure a):

A solution of dimethyl ester of adamantane-1,3-dicarboxylic acid (0.253 g, 1 mmol) in anhydrous THF (15 mL) was cooled to −60° C., and a suspension of [(CH$_3$OCH$_2$OH$_2$O)$_2$lH$_2$]Na (1.2 mL, 4 mmol) in anhydrous THF (5 mL) was added. After stirring for 1.5 hours, dilute H$_2$SO$_4$ (conc. H$_2$SO$_4$:H$_2$O=1:4) was added to the reaction mixture. The reaction mixture was warmed to ~10° C. and extracted with diethyl ether (3×20 mL). Combined organic phases were washed with saturated aqueous solution of NaCl (2×15 mL) and dried over anhydrous MgSO$_4$. Solvent was evaporated to give 0.505 g of the crude product which according to GC analysis (DB 210, 150° C.) consisted of the dicarbaldehyde (~45.6%). Crude dicarbaldehyde was chromatographed on a silica gel column using 0→50% of diethyl ether in pentane as eluent. During chromatography product decomposes and only a small part of the pure product was obtained. $^1$H NMR (CDCl$_3$) δ/ppm (300 MHz) 1.60-1.84 (m, 12H), 2.29 (br.s, 2H), 9.39 (s, 2H); $^{13}$C NMR (CDCl$_3$) δ/ppm (75 MHz) 26.6 (d, 2C), 34.2 (t, 1C), 35.0 (t, 4C), 35.3 (t, 1C), 44.5 (s, 2C), 204.4 (d, 2C); IR (KBr) ν$_{max}$/cm$^{-1}$ 2910 (s), 2850 (m), 2800 (w), 2700 (w), 1720 (s), 1450 (m).

Procedure b):

To a suspension of pyridinium chlorochromate (PCC, 0.850 g, 4.0 mmol) in CH$_2$Cl$_2$ (~10 mL) was added a suspension of 1,3-bis(hydroxymethyl)adamantane (0.196 g, 1.0 mmol) in anhydrous THF (~5 mL). The reaction mixture was stirred at room temperature for 2.5 hours, whereupon it was diluted with anhydrous diethyl ether (~50 mL) and filtered through a plug of florisil. The filtrate was evaporated in vacuo to afford dicarbaldehyde (0.183 g, 95%). According to GC analysis (DB 210, 150° C.), product had a purity of over 95%. Since dialdehyde is unstable and decomposes on silica gel, the sample was used in the next step without further purification.

Example 7

Anion Binding Test

NMR Titrations: To a 0.5 mL of the $CDCl_3$ solution of adamantane-dipyrromethane (c~0.05 M) was added an aliquot of the solution of $Bu_4NF$ (1 M in THF, containing <wt 5% $H_2O$) or $Bu_4NCl$, $Bu_4NBr$, $Bu_4NOAc$, $Bu_4NHSO_4$, $Bu_4NNO_3$ or $Bu_4NH_2PO_4$ (~0.5 M in $CDCl_3$), respectively. After each addition, NMR spectra were recorded. The titrations were performed at room temperature, 20° C.

Figure 2:
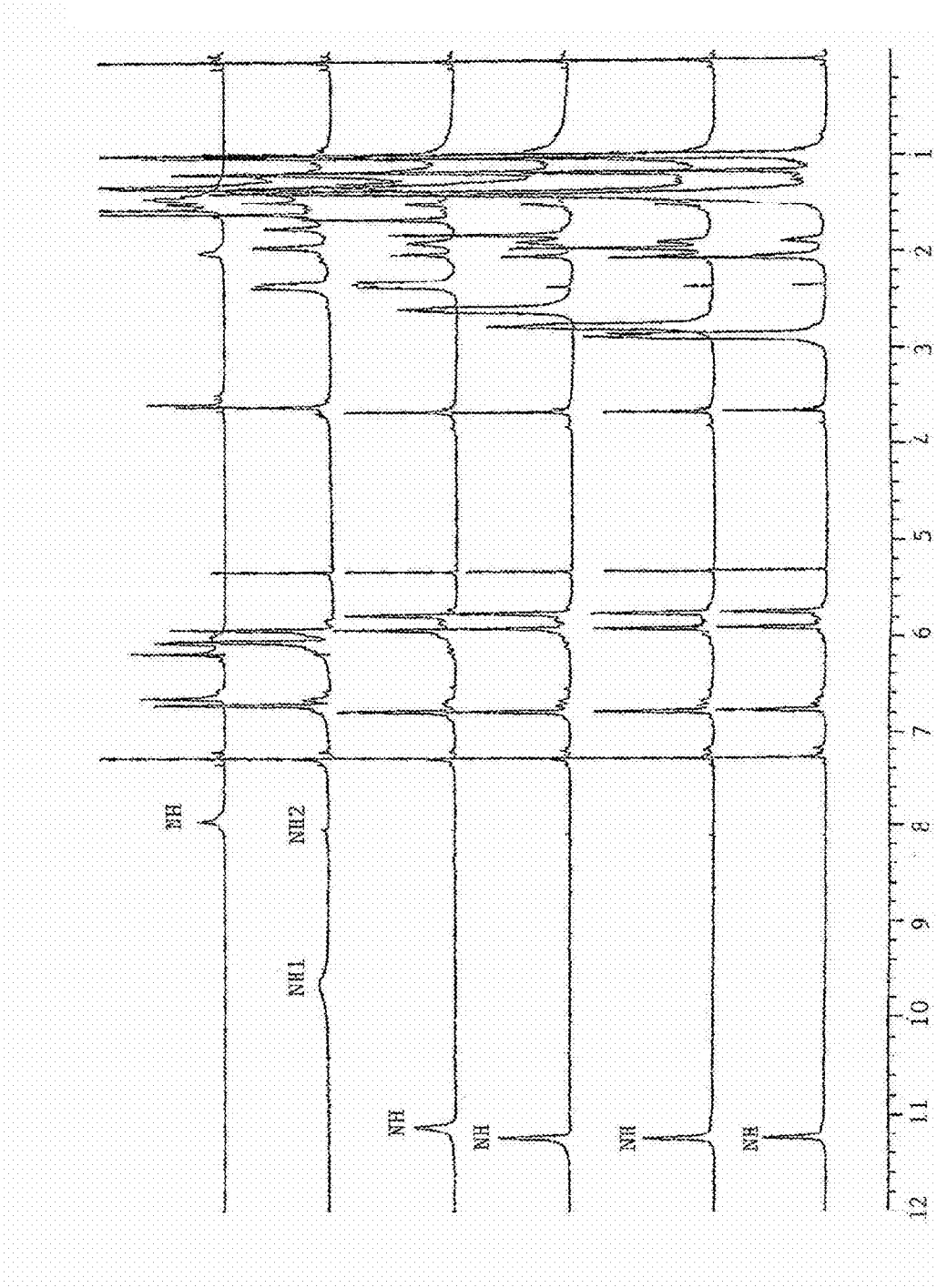
FIG. 2 illustrates $^1H$ NMR spectra ($CDCl_3$) of adamantane-dipyrromethane of general formula I, wherein $R_1$, $R_4$=di(pyrrole-2-yl)methyl and $R_2$, $R_3$, $R_5$-$R_9$=H (c=0.029 M) with increasing concentrations of $Bu_4NCl$.

Obtained results of the anion binding test are shown in FIGS. 1 and 2.

FIG. 1 illustrates $^1H$ NMR spectra ($CDCl_3$) of adamantane-dipyrromethane of general formula I, wherein $R_2$, $R_3$=pyrrole-2-yl and $R_1$, $R_4$-$R_9$=H (c=0.05 M) with increasing concentrations of $Bu_4NF$ (added as 1 M solution in THF). The top spectrum corresponds to the adamantane-dipyrromethane, while the spectra from the top to the bottom correspond to the adamantane-dipyrromethane and the following $F^-$ concentrations: 0.011, 0.022, 0.033, 0.044, 0.055, 0.066, 0.077, 0.088, and 0.11 M, respectively.

FIG. 2 illustrates $^1H$ NMR spectra ($CDCl_3$) of adamantane-dipyrromethane of general formula I, wherein $R_1$, $R_4$=di(pyrrole-2-yl)methyl and $R_2$, $R_3$, $R_5$-$R_9$=H (c=0.029 M) with increasing concentrations of $Bu_4NCl$. The top spectrum corresponds to the pure adamantane-dipyrromethane while the spectra from the top to the bottom correspond to the adamantane-dipyrromethane and the following $Cl^-$ concentrations: 0.00767, 0.0153, 0.0229, 0.0306 and 0.0383 M, respectively.

Example 8

Calixphyrine is obtained by reacting 1-di(pyrrole-2-yl)methyladamantane (60 mg, 0.2 mmol) with benzaldehyde (23 mg, 0.2 mmol) in the presence of TFA (1.5 μL, 0.02 mmol) in $CH_2Cl_2$ (20 mL). After stirring over 20 hours at room temperature, to the reaction mixture DDQ (48 mg, 0.2 mmol) was added and stirring continued for 1 hour. Solvent was evaporated and the residue (0.143 g) was chromatographed on a silica gel column using $CH_2Cl_2$ and $CH_2Cl_2$/diethyl ether as eluent to yield product (6 mg, 8%) as a yellow solid. $^1H$ NMR ($CDCl_3$, 300 MHz) δ 1.60-1.80 (m, 24H), 1.97 (br.s, 6H), 3.76 (5, 2H), 6.14-6.17 (m, 4H), 6.36-6.39 (m, 4H), 7.35-7.44 (m, 8H), 7.57-7.62 (m, 2H), 13.11 (5, 2H). $^{13}C$ NMR ($CDCl_3$, 75 MHz) δ28.9 (d, 60), 36.7 (t, 60), 38.6 (s, 20), 41.1 (t, 60), 54.3 (d, 2C), 119.9 (d, 4C), 127.1 (d, 2C), 127.2 (d, 2C), 127.7 (d, 4C), 128.2 (d, 2C), 130.7 (d, 2C), 130.8 (d, 2C), 137.8 (s, 2C), 139.2 (s, 2C), 140.2 (s, 80); IR (KBr) $v_{max}/cm^{-1}$ 3298 (5), 2900 (m), 2844 (m), 1584 (m), 720 (s). The following is a reaction scheme representing the use of adamantane-dipyrromethane described herein for the preparation of calixphyrine:

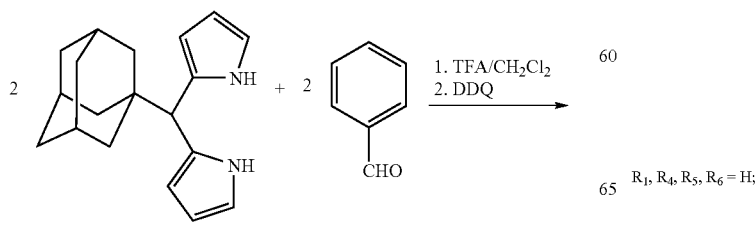

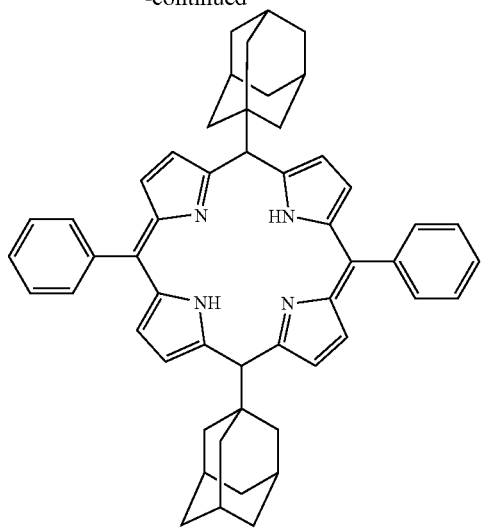

The invention claimed is:

1. A compound having general formula I,

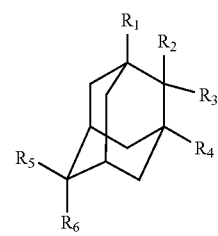

wherein $R_1$, $R_2$, $R_3$, $R_4$, $R_5$, and $R_6$ are defined according to one of the following combinations:

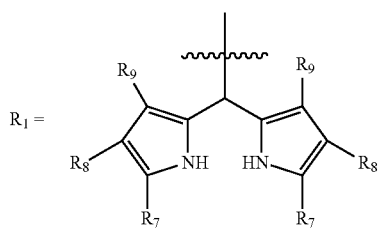

$R_2, R_3, R_4, R_5, R_6$ = H;

($R_1$ is dipyrromethane or substituted dipyrromethane and $R_2$, $R_3$, $R_4$, $R_5$, $R_6$ are hydrogen); or

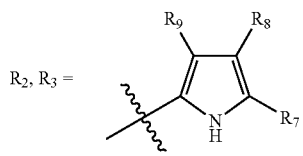

$R_1, R_4, R_5, R_6$ = H;

($R_2$ and $R_3$ are identical pyrroles or substituted pyrroles with identical $R_7$, $R_8$, and $R_9$ groups and $R_1$, $R_4$, $R_5$, $R_6$ are hydrogen), or

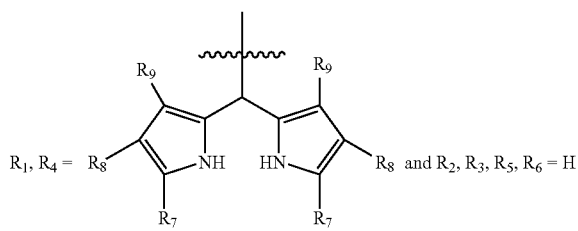

($R_1$ and $R_4$ are identical pyrroles or substituted pyrroles with identical $R_7$, $R_8$, and $R_9$ groups; and $R_2$, $R_3$, $R_5$, $R_6$ are hydrogen); or

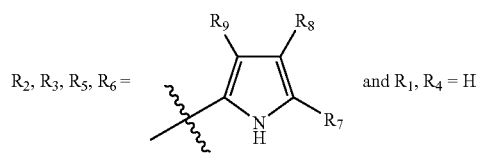

($R_2$, $R_3$, $R_5$, and $R_6$ are identical pyrroles or substituted pyrroles with identical $R_7$, $R_8$, and $R_9$ groups; and $R_1$ and $R_4$ are hydrogen);

wherein $R_7$, $R_8$, and $R_9$ are hydrogen, methyl, ethyl, propyl, butyl, pentyl, hexyl, vinyl, Cl, Br, CN, CHO, $CH_2OH$, $COOR_{10}$, or aryl, or their combination; and wherein $R_{10}$ is hydrogen, methyl, ethyl, tert-butyl, phenyl or benzyl; and wherein aryl has the general formula II,

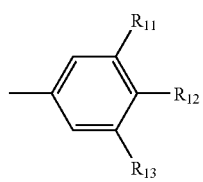

wherein $R_{11}$, $R_{12}$, $R_{13}$ are hydrogen, methyl, ethyl, propyl, methoxy, CN, F, Cl, or Br, or their combination.

2. A compound according to claim 1 wherein, $R_1$ is dipyrromethane or substituted dipyrromethane; and $R_2$, $R_3$, $R_4$, $R_5$, $R_6$ are hydrogen.

3. A compound according to claim 1 wherein, $R_2$ and $R_3$ are identical pyrroles or substituted pyrroles with identical $R_7$, $R_8$, and $R_9$ groups; and $R_1$, $R_4$, $R_5$, $R_6$ are hydrogen.

4. A compound according to claim 1 wherein, $R_1$ and $R_4$ are identical pyrroles or substituted pyrroles with identical $R_7$, $R_8$, and $R_9$ groups; and $R_2$, $R_3$, $R_5$, $R_6$ are hydrogen.

5. A compound according to claim 1 wherein, $R_2$, $R_3$, $R_5$, and $R_6$ are identical pyrroles or substituted pyrroles with identical $R_7$, $R_8$, and $R_9$ groups;

and $R_1$ and $R_4$ are hydrogen.

6. A process for the preparation of adamantane dipyrromethane derivative compounds having general formula I,

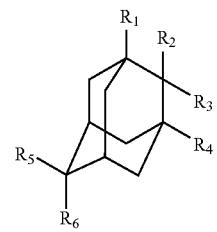

wherein $R_1$, $R_2$, $R_3$, $R_4$, $R_5$, and $R_6$ are defined according to one of the following combinations:

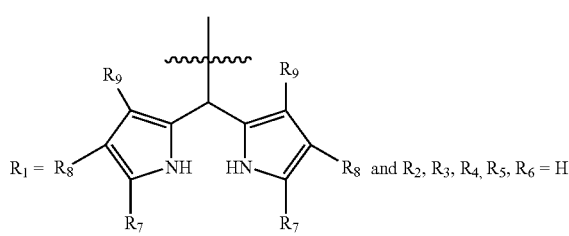

($R_1$ is dipyrromethane or substituted dipyrromethane and $R_2$, $R_3$, $R_4$, $R_5$, $R_6$ are hydrogen); or

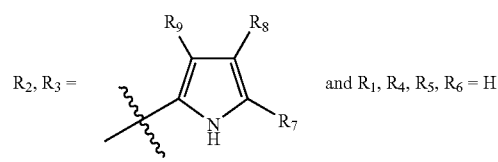

($R_2$ and $R_3$ are identical pyrroles or substituted pyrroles with identical $R_7$, $R_8$, and $R_9$ groups and $R_1$, $R_4$, $R_5$, $R_6$ are hydrogen), or

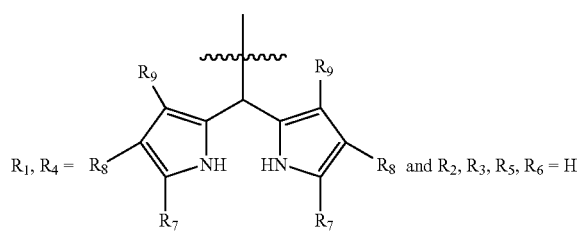

($R_1$ and $R_4$ are identical pyrroles or substituted pyrroles with identical $R_7$, $R_8$, and $R_9$ groups; and $R_2$, $R_3$, $R_5$, $R_6$ are hydrogen); or

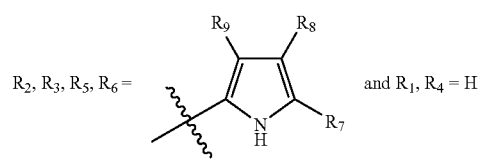

($R_2$, $R_3$, $R_5$, and $R_6$ are identical pyrroles or substituted pyrroles with identical $R_7$, $R_8$, and $R_9$ groups; and $R_1$ and $R_4$ are hydrogen);

wherein $R_7$, $R_8$, and $R_9$ are hydrogen, methyl, ethyl, propyl, butyl, pentyl, hexyl, vinyl, Cl, Br, CN, CHO, $CH_2OH$, $COOR_{10}$, or aryl, or their combination; and wherein $R_{10}$ is hydrogen, methyl, ethyl, tert-butyl, phenyl or benzyl; and wherein aryl has the general formula II,

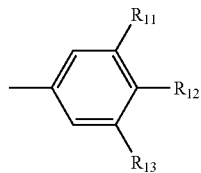

wherein $R_{11}$, $R_{12}$, $R_{13}$ are hydrogen, methyl, ethyl, propyl, methoxy, CN, F, Cl, or Br, or their combination; comprising:

condensation of a pyrrole or pyrrole derivative with carbonyl derivative, wherein carbonyl derivative comprises of adamantane-1-carbaldehyde, adamantane-2-one, adamantane-1,3-dicarbaldehyde and adamantane-2,6-dione, isolation of adamantane dipyrromethane derivative compounds by removal of acid by extraction using an aqueous base solution, extraction with an organic solvent, removal of the solvent and/or pyrrole by distillation, and purification by chromatography and/or crystallization.

7. The process for the preparation of adamantane dipyrromethane derivative compounds of claim 6, wherein adamantane-1,3-dicarbaldehyde is obtained by reducing the ester of adamantane-1,3-dicarboxylic acid or by oxidation of 1,3-bis(hydroxymethyl)adamantane.

8. The process for the preparation of adamantane dipyrromethane derivative compounds of claim 7, wherein reduction of the ester of adamantane-1,3-dicarboxylic acid is performed with $[(alkoxy)_2AlH_2]Na$ in nonaqueous diethyl ether or THF and wherein the extraction is performed with solvent comprising $CH_2Cl_2$, $CHCl_3$, diethyl ether, or ethyl acetate and chromatographic purification is performed on a column of silica gel using pentane/diethyl ether as solvent.

9. The process for the preparation of adamantane dipyrromethane derivative compounds of claim 8, wherein the oxidation of 1,3-bis(hydroxymethyl)adamantane is performed with reagent comprising of chromic acid, $MnO_2$, or PCC organic solvent comprising $CH_2Cl_2$, $CHCl_3$, THF, diethyl ether, and wherein purification is performed comprising filtration through florisil using THF or diethyl ether as solvent.

10. A chemical mixture used for anion detection in chemical and biochemical processes comprising at least one compound of claim 1.

11. A method of binding anions using the compound of claim 1, comprising the steps:
   (a) adding an aliquot of anion solution to the solution of compound I;
   (b) recording the NMR spectra of after the addition of said anion aliquot;
   (c) comparing the recorded NMR spectra with each repetition of steps (a) and (b);
   (d) detecting a signal shift in NMR spectra to the lower magnetic field caused by increasing anion concentration in titration solution.

12. A method of preparing calixphirins using the compound of claim 1, comprising the following steps:
   (a) reacting of compound I with benzaldehyde in the presence of TFA in $CH_2Cl_2$;
   (b) adding DDQ to the reaction mixture;
   (c) evaporating the solvent to obtain a residue;
   (d) conducting chromatography of the residue on a silica gel column using $CH_2Cl_2$ and $CH_2Cl_2$/diethyl ether as eluent to yield a calixphirine.

* * * * *